US010165833B2

(12) United States Patent
Pariseau et al.

(10) Patent No.: US 10,165,833 B2
(45) Date of Patent: Jan. 1, 2019

(54) MECHANICAL FASTENER, FASTENING SYSTEM, AND DISPOSABLE ABSORBENT ARTICLE (75) Inventors: Timothy P. Pariseau, Forest Lake, MN (US); Michael R. Gorman, Lake Elmo, MN (US); Shin Katoh, Kanagawa-prefecture (JP); Tadato Oritani, Kanagawa (JP); Zhiqun Zhang, Roseville, MN (US); Neelakandan Chandrasekaran, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 477 days.

(21) Appl. No.: 14/344,648

(22) PCT Filed: Sep. 13, 2012

(86) PCT No.: PCT/US2012/055072
§ 371 (c)(1),
(2), (4) Date: Mar. 13, 2014

(87) PCT Pub. No.: WO2013/040156
PCT Pub. Date: Mar. 21, 2013

(65) Prior Publication Data
US 2014/0350507 A1  Nov. 27, 2014

Related U.S. Application Data (60) Provisional application No. 61/654,492, filed on Jun. 1, 2012, provisional application No. 61/535,639, filed on Sep. 16, 2011.

(51) Int. Cl.
*A44B 18/00* (2006.01)
*A61F 13/496* (2006.01)
*A61F 13/62* (2006.01)

(52) U.S. Cl.
CPC ........ *A44B 18/0019* (2013.01); *A61F 13/496* (2013.01); *A61F 13/625* (2013.01); *Y10T 24/27* (2015.01)

(58) Field of Classification Search
CPC ............ A44B 18/0019; A44B 18/0049; A44B 18/0065; A61F 13/496; A61F 13/62; A61F 13/625; Y10T 24/2792
See application file for complete search history.

(56) References Cited

U.S. PATENT DOCUMENTS 4,775,310 A   10/1988  Fischer
4,839,131 A    6/1989  Cloeren
(Continued)

FOREIGN PATENT DOCUMENTS

EP   341993   11/1989
EP   539504    5/1993
(Continued)

OTHER PUBLICATIONS

US 5,389,416, 02/1995, Mody (withdrawn)
International Search Report for PCT International Application No. PCT/US2012/055072, dated Dec. 7, 2012, 4 pages.

*Primary Examiner* — Robert Sandy
*Assistant Examiner* — Rowland Do (57) ABSTRACT A mechanical fastener is disclosed that includes a thermoplastic backing and multiple, upstanding fastening elements that have a post with a proximal end attached to the thermoplastic backing and a distal end comprising a cap larger in area than a cross-sectional area of the post. The basis weight of the mechanical fastener is in a range from 25 grams per square meter to 75 grams per square meter, and the height of the multiple, upstanding fastening elements is
(Continued)

up to 300 micrometers. Fastening systems and disposable absorbent articles including the mechanical fastener are also disclosed.

20 Claims, 1 Drawing Sheet

(56) References Cited

U.S. PATENT DOCUMENTS

| | | | |
|---|---|---|---|
| 4,846,815 A | 6/1989 | Scripps | |
| 4,894,060 A * | 1/1990 | Nestegard | A44B 18/0053 |
| | | | 128/DIG. 15 |
| 5,325,569 A | 7/1994 | Goulait | |
| 5,326,612 A * | 7/1994 | Goulait | A44B 18/0011 |
| | | | 24/450 |
| 5,392,498 A | 2/1995 | Goulait | |
| 5,531,732 A | 7/1996 | Wood | |
| 5,537,723 A | 7/1996 | Yoshida | |
| 5,569,233 A | 10/1996 | Goulait | |
| 5,607,635 A | 3/1997 | Melbye | |
| 5,755,016 A | 5/1998 | Provost | |
| 5,845,375 A * | 12/1998 | Miller | A41D 13/1161 |
| | | | 24/452 |
| 5,858,515 A * | 1/1999 | Stokes | A44B 18/0011 |
| | | | 156/167 |
| 5,868,987 A * | 2/1999 | Kampfer | A44B 18/0061 |
| | | | 24/442 |
| 5,961,761 A * | 10/1999 | Heindel | A61F 13/15756 |
| | | | 156/163 |
| 6,035,498 A | 3/2000 | Buzzell | |
| 6,054,091 A | 4/2000 | Miller | |
| 6,075,179 A | 6/2000 | McCormack | |
| 6,106,922 A | 8/2000 | Cejka | |
| 6,132,660 A * | 10/2000 | Kampfer | A44B 18/0049 |
| | | | 24/442 |
| 6,163,939 A | 12/2000 | Lacey | |
| 6,190,594 B1 | 2/2001 | Gorman | |
| 6,190,758 B1 | 2/2001 | Stopper | |
| 6,368,097 B1 | 4/2002 | Miller | |
| 6,588,073 B1 * | 7/2003 | Zoromski | A44B 18/0015 |
| | | | 24/446 |
| 6,708,378 B2 * | 3/2004 | Parellada | A44B 18/0049 |
| | | | 24/304 |
| 6,767,492 B2 | 7/2004 | Norquist | |
| 6,770,065 B1 | 8/2004 | Sasaki | |
| 6,899,841 B2 | 5/2005 | Buzzell | |
| 6,904,649 B2 | 6/2005 | Van Benschoten | |
| 7,067,185 B2 | 6/2006 | Ausen | |
| 7,162,780 B2 | 1/2007 | Martin | |
| 7,168,139 B2 | 1/2007 | Seth | |
| 7,185,401 B2 | 3/2007 | Ausen | |
| 7,214,334 B2 | 5/2007 | Jens | |
| 7,241,483 B2 | 7/2007 | Ausen | |
| 7,444,722 B2 * | 11/2008 | McDaniel | A44B 18/0015 |
| | | | 24/446 |
| 7,748,090 B2 | 7/2010 | Seth | |
| 7,897,078 B2 | 3/2011 | Petersen | |
| 9,084,701 B2 | 7/2015 | RamosMedina | |
| 2001/0014350 A1 * | 8/2001 | Krzysik | A61K 8/0208 |
| | | | 424/443 |
| 2001/0031954 A1 * | 10/2001 | Jordan | A61F 13/42 |
| | | | 604/385.01 |
| 2002/0007148 A1 * | 1/2002 | May | A61F 13/49009 |
| | | | 604/132 |
| 2002/0035354 A1 * | 3/2002 | Mirle | A61F 13/5146 |
| | | | 604/385.01 |
| 2002/0095131 A1 * | 7/2002 | Olson | A61F 13/15756 |
| | | | 604/391 |
| 2002/0124359 A1 | 9/2002 | Murasaki | |
| 2002/0138064 A1 | 9/2002 | Datta | |
| 2002/0143316 A1 * | 10/2002 | Sherrod | A61F 13/505 |
| | | | 604/385.101 |
| 2002/0165514 A1 * | 11/2002 | Datta | A61F 13/4702 |
| | | | 604/385.01 |
| 2003/0182776 A1 | 10/2003 | Ausen | |
| 2004/0068848 A1 * | 4/2004 | Ausen | A44B 18/0049 |
| | | | 24/452 |
| 2004/0111844 A1 | 6/2004 | Ausen | |
| 2004/0187276 A1 | 9/2004 | Seth | |
| 2005/0101926 A1 | 5/2005 | Ausen | |
| 2008/0140043 A1 | 6/2008 | Mandzsu | |
| 2008/0249496 A1 * | 10/2008 | Petersen | A61F 13/15756 |
| | | | 604/385.03 |

FOREIGN PATENT DOCUMENTS

| | | |
|---|---|---|
| GB | 2397620 | 7/2004 |
| JP | 11-155612 | 6/1999 |
| JP | 2011-152947 | 8/2011 |
| WO | WO 1994-04053 | 3/1994 |
| WO | WO 1998-57565 | 12/1998 |
| WO | WO 2003-059108 | 7/2003 |
| WO | WO 2003-059110 | 7/2003 |
| WO | WO 2006-101844 | 9/2006 |

\* cited by examiner

MECHANICAL FASTENER, FASTENING SYSTEM, AND DISPOSABLE ABSORBENT ARTICLE

CROSS-REFERENCE TO RELATED APPLICATIONS

This application is a national stage filing under 35 U.S.C. 371 of PCT/US2012/055072, filed Sep. 13, 2012, which claims priority to U.S. Provisional Application Nos. 61/535,639, filed Sep. 16, 2011, and 61/654,492, filed Jun. 1, 2012, the disclosures of which are incorporated by reference in their entirety herein.

BACKGROUND

Mechanical fasteners, which are also called hook and loop fasteners, typically include a plurality of closely spaced upstanding projections with loop-engaging heads useful as hook members, and loop members typically include a plurality of woven, nonwoven, or knitted loops. Mechanical fasteners are useful for providing releasable attachment in numerous applications. For example, mechanical fasteners are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Mechanical fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

Hook and loop fastening systems can include at least two engagement strength characteristics: peel strength and shear strength. Peel strength corresponds to the force required to disengage the fastening members from one another by peeling one fastening member upward and away from the other fastening member. Shear strength corresponds to the force required to disengage the fastening members from one another by pulling at least one of the fastening members away from the other in a plane that is parallel to the fastening members. Typically, the engagement strength of the fastening members is higher in shear than in peel. While the peel strength may be a factor when the fastening members are intentionally separated, typically, the shear strength is responsible for holding the fastening members together during normal use.

SUMMARY

The present disclosure provides a mechanical fastener with a relatively low basis weight compared to conventional mechanical fasteners and fastening systems and also provides disposable absorbent articles that contain the mechanical fastener. Decreasing the basis weight of the mechanical fastener results in lower manufacturing cost and advantageously decreases the amount of thermoplastic that is discarded, for example, when a disposable absorbent article including the mechanical fastener is thrown away. Despite its low basis weight, the mechanical fastener disclosed herein has comparable or better engagement to loop materials than higher-basis-weight mechanical fasteners as measured by shear and peel testing. High engagement to loop materials is observed even for so-called low-loft loop materials, which are being used more frequently for disposable absorbent articles to decrease cost and the amount of material on the disposable absorbent article. Thus, the mechanical fasteners disclosed herein can be considered to have a high material efficiency. Typically, the mechanical fasteners disclosed herein are also soft to the touch on both the first surface having the upstanding fastening elements and the second, opposing surface.

In one aspect, the present disclosure provides a mechanical fastener including a thermoplastic backing and multiple, upstanding fastening elements that have a post with a proximal end attached to the thermoplastic backing and a distal end with a cap larger in area than a cross-sectional area of the post. The basis weight of the mechanical fastener is in a range from 25 grams per square meter to 75 grams per square meter, and the height of the multiple, upstanding fastening elements is up to 300 micrometers. In some embodiments, the basis weight of the mechanical fastener may be 40 grams per square meter (gsm) to 75 gsm, 50 gsm to 75 gsm, or 55 to 70 gsm.

In another aspect, the present disclosure provides a fastening system including the mechanical fastener described above and a loop material for engaging with the mechanical fastener. In some embodiments, the basis weight of the fiber of the loop material is in a range from 10 grams per square meter to 30 grams per square meter.

In another aspect, the present disclosure provides a disposable absorbent article that includes the mechanical fastener or the fastening system described above.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The term "upstanding" refers to posts that protrude from the thermoplastic backing and includes posts that stand perpendicular to the backing and posts that are at an angle to the backing other than 90 degrees.

The term "multiple" means more than one and can include any desired number of upstanding fastening elements.

The terms "first" and "second" are used in this disclosure in their relative sense only. It will be understood that, unless otherwise noted, those terms are used merely as a matter of convenience in the description of one or more of the embodiments.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Figure 1:
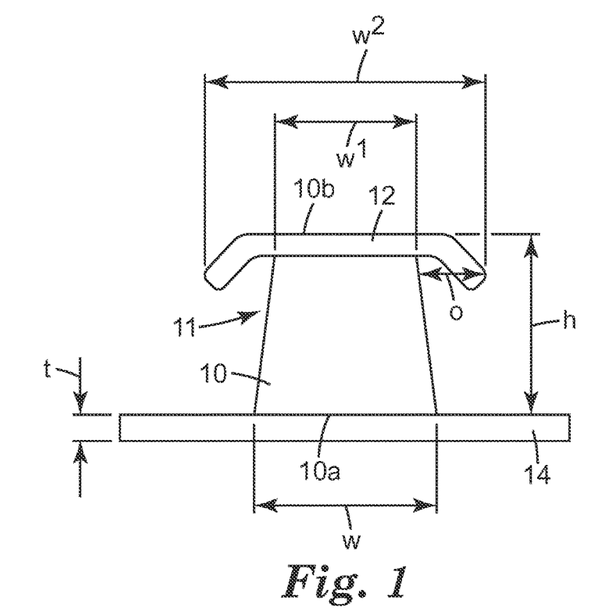
FIG. 1 is a side view of an exemplary upstanding fastening element on a thermoplastic backing useful in the mechanical fastener disclosed herein, wherein the various dimensions of the upstanding fastening element are shown.

Referring to FIG. 1, the mechanical fastener according to the present disclosure includes a thermoplastic backing 14 with multiple, upstanding fastening elements 11 attached to the thermoplastic backing 14. As shown in the embodiment illustrated in FIG. 1, the multiple, upstanding fastening elements 11 have posts 10 with proximal ends 10a attached to the thermoplastic backing 14 and distal ends 10b comprising a cap 12 with a larger area than a cross-sectional area of the post 10. Cap 12 extends an overhang distance "o" beyond the post. The height "h" of the upstanding fastening element is the distance between the thermoplastic backing 14 and the distal end 10b of the upstanding fastening element 11 as shown in FIG. 1. The thickness "t" of the thermoplastic backing 14, the width "w" of the post at its base, the width "$w^1$" of the post just below the cap, and the width "$w^2$" of the cap are also shown in FIG. 1.

Various factors influence the basis weight of a mechanical fastener. For example, the use of lower-density thermoplastic polymers will decrease the basis weight of the mechanical fastener. Furthermore, the height "h" and width "w" of the upstanding fastening elements influences the amount of material in the mechanical fastener and therefore influences its basis weight. In the illustrated embodiment, the amount of material in the cap, which relates to cap width "$w^2$", also influences the basis weight. The thickness of the backing "t" tends to have a large influence on the basis weight of the mechanical fastener. Typically, the thickness of the backing "t" in the mechanical fastener disclosed herein is in a range from 20 micrometers (μm) to 80 μm. In some embodiments, the thickness of the backing "t" is in a range from 30 μm to 75 μm, 40 μm to 75 μm, 20 μm to 70 μm, or 30 μm to 70 μm. For the purposes of this application, all dimensions of the upstanding fastening elements described herein with reference to FIG. 1 and in the claims are measured by optical microscopy.

The height "h" of the upstanding fastening elements is low enough to keep the basis weight at 75 gsm or below and provides excellent engagement to loop materials (e.g., low-loft loop materials). In the mechanical fastener according to the present disclosure, the upstanding fastening elements 11 have a maximum height "h" of up to 300 μm, in some embodiments up to 285 μm, 275 μm, or 250 μm. In some embodiments, the mechanical fastener according to the present disclosure has upstanding fastening elements 11 with a minimum height "h" of at least 40 μm, in some embodiments, at least 50 μm, 100 μm, or 140 μm. In some embodiments, the mechanical fastener according to the present disclosure has upstanding fastening elements 11 with a height "h" in a range from 150 μm to 300 μm, 40 μm to 285 μm, 100 μm to 275 μm, 140 μm to 250 μm, 50 μm to 300 μm, 50 μm to 285 μm, 50 μm to 275 μm, 100 μm to 250 μm, 100 μm to 285 μm, 100 μm to 300 μm, 140 μm to 275 μm, or 155 μm to 250 μm.

Typically, the upstanding fastening elements 11 in the mechanical fastener according to the present disclosure have aspect ratio (that is, a ratio of height "h" over the widest width dimension "w") of up to about 2:1, 1.5:1, or 1.2:1. The posts 10 may have a cross-section with a maximum width dimension "w" of up to 250 μm and at least 100 μm. In some embodiments, the posts 10 have a cross-section with a width dimension "w" in a range from 125 μm to 200 μm or 135 μm to 190 μm. The term "width dimension" should be understood to include the diameter of a post 10 with a circular cross-section. When the post 10 has more than one width dimension (e.g., in a rectangular or elliptical cross-section shaped post), the aspect ratio described herein is the height over the largest width dimension.

In the mechanical fastener according to the present disclosure, the upstanding fastening elements 11, which may be made, for example, by any of the methods described below, may have a post 10 that tapers, for example, from the proximal end 10a toward the distal end 10b. The proximal end 10a may have a larger width dimension "w" than the post 10 adjacent the cap 12, where the width dimension is "$w^1$" shown in FIG. 1. In some embodiments, the posts 10 have a width dimension "$w^1$" immediately under the cap in a range from 100 μm to 200 μm, 120 μm to 195 μm, or 130 μm to 185 μm. The tapering may facilitate the removal of the post 10 from the mold surface in the methods described below. Again, the aspect ratio described above is the height "h" over the largest width dimension "w".

The mechanical fastening elements described herein have caps that are typically larger in area than the cross-sectional area of the posts. In some embodiments, the cross-section area of the post is measured just below the cap (e.g., at the point where width "$w^1$" is shown). Furthermore, a ratio of a width dimension of the formed cap to the post measured at the proximal end is typically at least 1.01:1 or 1.2:1 and may be up to 2:1. Referring again to FIG. 1, the caps 12 may have a maximum width dimension "$w^2$" of up to 380 μm and at least 150 μm. In some embodiments, the caps 12 have a width dimension "$w^2$" in a range from 150 μm to 350 μm or 170 μm to 340 μm. The width dimension "$w^2$" is measured by viewing the caps from above. The term "width dimension" should be understood to include the diameter of a cap 12 with a circular cross-section. When the cap 12 has more than one width dimension (e.g., in a rectangular or elliptical cross-section shaped cap), "$w^2$" is measured at the widest point of the cap 12.

The width "$w^2$" of the cap 12 and the width of the post 10 toward the distal end 10b are related to the cap overhang "o". Specifically, the cap overhang "o" in the illustrated embodiment is calculated from the formula (cap width "$w^2$"—post width at the distal end) divided by 2. In some embodiments of the mechanical fasteners according to the present disclosure, the overhang distance is up to 90 μm. In other words, the overhang extends up to 90 μm beyond the post. In some embodiments, the overhang is up to 85, 84 μm, 82 μm, or 80 μm. The minimum amount of overhang may be selected, for example, based on the fiber diameter of the loop that is selected to engage with the mechanical fastener disclosed herein. In some embodiments, the overhang is at least 5 μm or 10 μm. The overhang may be in the range, for example, from 5 μm to 84 μm, 5 μm to 80 μm, or 5 μm to 75 μm. For embodiments in which the mechanical fastener disclosed herein is used for pad fixation (e.g., in an adult incontinence article as described below), the overhang may be in the range, for example, from 5 μm to 65 μm.

Mechanical fasteners according to the present disclosure having upstanding fastening elements with a ratio of overhang distance, calculated as described above, to height "h". The ratio relates to how much the cap or the post will bend when the upstanding fastening element is exposed to a shear force and therefore is referred to here for convenience as the "bending index". In some embodiments of the mechanical fastener disclosed herein, the upstanding fastening elements have a bending index of up to 0.6, 0.50, or 0.45. For example, the upstanding fastening elements may have a bending index of 0.02 to 0.6 or 0.05 to 0.5. For a bending index below 0.02, the post may bend when the mechanical fastener is exposed to a shear force, decreasing the strength of engagement. For a bending index greater than 0.6, the cap may bend when the mechanical fastener is exposed to a shear force, decreasing the strength of engagement.

Many thermoplastic materials are useful for mechanical fasteners according to the present disclosure. Suitable thermoplastic materials for the thermoplastic backing with upstanding fastening elements include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; poly(acrylonitrile-butadiene-styrene); plasticized polyvinylchlorides; and mixtures thereof. Typically, the thermoplastic is a polyolefin (e.g., polyethylene, polypropylene, polybutylene, ethylene copolymers, propylene copolymers, butylene copolymers, and copolymers and blends of these materials). The various thermoplastic materials described above can be formulated into a master batch having a desired property (e.g., color); however, the presence or absence of dyes, pigments, or other colorants are not essential to this disclosure.

In some embodiments, the thermoplastic backing with upstanding fastening elements can be made from a multilayer or multi-component melt stream of thermoplastic materials. This can result in fastening elements formed at least partially from a different thermoplastic material than the one predominately forming the backing. Various configurations of upstanding posts made from a multilayer melt stream are shown in U.S. Pat. No. 6,106,922 (Cejka et al.), for example. A multilayer or multi-component melt stream can be formed by any conventional method. A multilayer melt stream can be formed by a multilayer feedblock, such as that shown in U.S. Pat. No. 4,839,131 (Cloeren). A multicomponent melt stream having domains or regions with different components could also be used. Useful multicomponent melt streams could be formed by use of inclusion co-extrusion die or other known methods (e.g., that shown in U.S. Pat. No. 6,767,492 (Norquist et al.).

In the mechanical fasteners according to the present disclosure the thermoplastic backing and the upstanding posts are typically integral (that is, formed at the same time as a unit, unitary). In some embodiments, the thermoplastic backing and the upstanding fastening elements are made from the same thermoplastic material. The thermoplastic backing is typically in the form of a sheet or web that may have an essentially uniform thickness with the upstanding fastening elements directly attached to the thermoplastic backing. Upstanding posts on a backing can be made, for example, by conventional extrusion through a die and cast molding techniques. In some embodiments, a thermoplastic material is fed onto a continuously moving mold surface with cavities having the inverse shape of the upstanding posts. The height of the posts is determined by the depth of the cavities. The thermoplastic material can be passed between a nip formed by two rolls or a nip between a die face and roll surface, with at least one of the rolls having the cavities (i.e., at least one of the rolls is a tool roll). Pressure provided by the nip forces the resin into the cavities. In some embodiments, a vacuum can be used to evacuate the cavities for easier filling of the cavities. The nip has a gap that is typically sufficiently big such that a coherent backing is formed over the cavities. The mold surface and cavities can optionally be air or water cooled before stripping the integrally formed backing and upstanding posts from the mold surface such as by a stripper roll.

Suitable tool rolls can be made, for example, by forming (e.g., by computer numerical control with drilling, photo etching, using galvanic printed sleeves, laser drilling, electron beam drilling, metal punching, direct machining, or lost wax processing) a series of holes having the inverse shape of the upstanding posts into the cylindrical face of a metal mold or sleeve. Other suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Still other suitable tool rolls may include wire-wrapped rolls, which are disclosed along with their method of manufacturing, for example, in U.S. Pat. No. 6,190,594 (Gorman et al.). The exposed surface of the mold, sleeve, plate, or wire may be coated to impart surface properties such as increased wear resistance, controlled release characteristics, and controlled surface roughness. The coating, if present, is preferably selected so that the adhesion of the thermoplastic material to the tool roll is less than the cohesion of the thermoplastic material at the time of the removal of the thermoplastic backing from the tool roll.

Another exemplary method for forming a thermoplastic backing with upstanding posts includes using a flexible mold belt defining an array of upstanding post-shaped cavities as described in U.S. Pat. No. 7,214,334 (Jens et al.). The mold belt is trained about first and second rolls, and a source of molten thermoplastic material is arranged to deliver the thermoplastic to the mold belt. The apparatus is constructed to force the plastic resin into the upstanding post-shaped cavities of the belt under pressure in a gap to mold the array of upstanding posts while forming the thermoplastic web layer.

Useful upstanding posts on a backing may have a variety of heights above the backing, which may be changed, for example, after a capping process described below to provide the upstanding fastening elements of the mechanical fastener described herein. For example, the upstanding posts can have a maximum height (above the backing) of up to 400 micrometers (μm), in some embodiments up to 350 μm or 300 μm. The upstanding posts can have a minimum height of at least 150 μm, in some embodiments, at least 160 μm or 175 μm. Useful upstanding posts according to the present disclosure can have a height in a range from 150 μm to 400 μm or 150 μm to 350 μm.

Posts formed upon exiting the cavities typically do not have caps, but they can be subsequently formed into upstanding fastening elements described herein by a capping method as described in U.S. Pat. No. 5,607,635 (Melbye et al.). Typically, the capping method includes deforming the tip portions of the upstanding posts using heat and/or pressure. The heat and pressure, if both are used, could be applied sequentially or simultaneously. In some embodiments, deforming comprises contacting the distal tips of the upstanding posts with a heated surface. The heated surface may be a flat surface or a textured surface such as that disclosed in U.S. Pat. No. 6,708,378 (Parellada et al.) or U.S. Pat. No. 5,868,987 (Kampfer et al.). In some embodiments, wherein the thermoplastic backing with upstanding fastening elements is a web of indefinite length, deforming the distal tips of the posts to form caps includes moving the web in a first direction through a nip having a heated surface member and an opposing surface member such that the heated surface member contacts the distal tips. In these embodiments, the heated surface may be, for example, a capping roll. In some embodiments, the surfaces used to contact the distal tips may not be heated. In these embodiments, the deformation is carried out with pressure and without heating. In some embodiments, the heated surface may be a heated roll opposite a curved support surface forming a variable nip having a variable nip length as described, for example, in U.S. Pat. No. 6,368,097 (Miller et al.). The curved support surface may curve in the direction of the heated roll, and the heated roll may include a feeding mechanism for feeding the thermoplastic backing with upstanding posts through the variable nip to compressively engage the web between the heated roll and the support surface. In some embodiments, heating is carried out below a melt temperature of the distal tips. When the thermoplastic material used to form the upstanding posts is a copolymer (e.g., copolymers of ethylene and propylene), the distal tips may have more than one melt temperature. In these embodiments, "below a melt temperature of the distal tips" means below at least one of the melt temperatures.

In some embodiments, distal caps of the upstanding fastening elements are reshaped after they are formed. For example, passing a thermoplastic backing having upstanding capped posts through a gapped nip of a heated rubber roll and a backup roll causes the overhanging portions of the distal cap, that extend beyond the post, to be pushed down toward the backing. This process is described in U.S. Pat. No. 6,132,660 (Kampfer).

In addition to the continuous methods described above, it is also envisioned that thermoplastic backings having upstanding fastening elements can be prepared using batch processes (e.g., single piece injection molding). The thermoplastic backing may have any suitable dimension, but length (L) and width (W) dimensions of at least 10 centimeters may be useful.

Another method for forming a thermoplastic backing with upstanding fastening elements is profile extrusion, which is described, for example, in U.S. Pat. No. 4,894,060 (Nestegard). Typically, in this method a thermoplastic flow stream is passed through a patterned die lip (e.g., cut by electron discharge machining) to form a web having downweb ridges. The ridges can then be transversely sliced at spaced locations along the extension of the ridges to form upstanding fastening elements with a small separation caused by the cutting blade. The separation between upstanding fastening elements is then increased by stretching. However, it should be understood that "upstanding fastening elements" do not include such ridges before they are cut. Such ridges themselves would not be considered to have a "loop-engaging overhang" because they would not be able to engage loops before they are cut and stretched. In some embodiments, the mechanical fasteners according to the present disclosure are not made by profile extrusion.

In the mechanical fastener according to the present disclosure, the upstanding fastening elements, which may be made, for example, by any of the methods described above, may have a variety of cross-sectional shapes. For example, the cross-sectional shape of the post may be a polygon (e.g., square, rectangle, hexagon, or pentagon), which may be a regular polygon or not, or the cross-sectional shape of the post may be curved (e.g., round or elliptical). In some embodiments, the posts taper and decrease in size from the proximal ends toward the distal ends.

Generally, the distal ends of the upstanding fastening elements have a shape that is different from the shape of the post. For example, the fastening element may be in the shape of a mushroom (e.g., with a circular or oval head enlarged with respect to the post), a nail, or a T. Upstanding fastening element having these shapes are typically considered multi-directional. In some of these embodiments, the overhang extends beyond the posts on at least two opposing sides of the post. The extent of overhang on the two opposing sides may or may not be equal. In some of these embodiments, the fastening element is in the shape of a mushroom (e.g., with a circular or oval head enlarged with respect to the post) or a nail. In upstanding fastening elements having caps, the caps may have at least a portion of the overhang in all directions although the amount of overhang may not be equal in all directions.

The overhang in the upstanding fastening elements disclosed herein is typically considered to be loop-engaging. The term "loop-engaging" as used herein relates to the ability of an upstanding fastening element to be mechanically attached to a loop material. The loop-engageability of hook elements may be determined and defined by using standard woven, nonwoven, or knit materials. A region of posts with loop-engaging overhangs the distal ends generally will provide, in combination with a loop material, at least one of a higher peel strength, higher dynamic shear strength, or higher dynamic friction than a region of posts without loop-engaging overhangs.

The thermoplastic backing may have an essentially uniform cross-section, or the thermoplastic backing may have additional structure beyond what is provided by the upstanding fastening elements, which may be imparted, for example, by at least one of the forming rolls described above.

In some embodiments, the thickness of the thermoplastic backing in a range from 20 µm to 80 µm is achieved for the mechanical fastener disclosed herein by the gap of the nip between two rolls or the die face and a roll in the extrusion and cast molding process described above. An endless metal or polymer belt or a metal belt coated with polymer may be useful to provide even pressure in the nip.

In some embodiments, the mechanical fastener according to the present disclosure is made by a method that includes stretching the initially formed thermoplastic backing to achieve a backing thickness in a range from 20 µm to 80 µm. Stretching can be carried out on a web biaxially or monoaxially. Biaxial stretching means stretching in two different directions in the plane of the thermoplastic backing. Typically, but not always, one first direction is the longitudinal direction "L", and one second direction is the width direction "W". Biaxial stretching can be performed sequentially by stretching the thermoplastic backing, for example, first in one of the first or second direction and subsequently in the other of the first or second direction. Biaxial stretching can also be performed essentially simultaneously in both directions. Monoaxial stretching refers to stretching in only one direction in the plane of the thermoplastic backing. Typically, monoaxial stretching is performed in one of the "L" or "W" direction but other stretch directions are also possible.

In some embodiments, the stretching increases at least one of the thermoplastic backing's length ("L") or width ("W") at least 1.5 times (in some embodiments, at least 2, 2.5, or 3 times). In some embodiments, the stretching increases both of the thermoplastic backing's length ("L") and width ("W") at least 1.5 times (in some embodiments, at least 2, 2.5, or 3 times). In some embodiments, the stretching increases at least one of the thermoplastic backing's length ("L") or width ("W") up to 7 or 5 times). In some embodiments, the stretching increases both of the thermoplastic backing's length ("L") and width ("W") up to 7 or 5 times. Stretching can be carried out to an extent so that the desired basis weight of the mechanical fastener can be achieved.

In some embodiments, the stretching is carried out at least to the natural stretch ratio. When a thermoplastic film (e.g., a thermoplastic backing as described herein) is monoaxially or biaxially stretched at a temperature below the melting point of the thermoplastic material, particularly at a temperature below the line drawing temperature of the film, the thermoplastic film may stretch non-uniformly, and a clear boundary is formed between stretched and unstretched parts. This phenomenon is referred to as necking or line drawing. However, substantially the entire thermoplastic backing is stretched uniformly when it is stretched to a sufficiently high degree. The stretch ratio at which this occurs is referred to as the "natural stretch ratio" or "natural draw ratio." The natural stretch ratio may be defined, for example, as the stretch ratio where the relative standard deviation of local stretch ratios measured at a variety of locations on the thermoplastic backing is below about 15 percent. Stretching above the natural stretch ratio tends to provide significantly more uniform properties or characteristics such as thickness, tensile strength, and modulus of elasticity. For any given thermoplastic backing and stretch conditions, the natural stretch ratio is determined by factors such as the composition of the thermoplastic resin forming the thermoplastic backing, the morphology of the formed thermoplastic backing due to quenching conditions on the tool roll, for example, and temperature and rate of stretching. Furthermore, for biaxially stretched thermoplastic backings, the natural stretch ratio in one direction will be affected by the stretch conditions, including final stretch ratio, in the other direction. Thus, there may be said to be a natural stretch ratio in one direction given a fixed stretch ratio in the other, or, alternatively, there may be said to be a pair of stretch ratios (one in the first direction and one in the second direction) which result in the natural stretch ratio. The term "stretch ratio" refers to a ratio of a linear dimension of a given portion of the thermoplastic backing after stretching to the linear dimension of the same portion before stretching.

In some embodiments, stretching is carried out to an extent below the natural stretch ratio of the thermoplastic backing. In some of these embodiments, the thermoplastic backing is stretched to a ratio in a range from 1.5 to 4 in one direction (e.g., the machine direction).

When the thermoplastic backing is a web of indefinite length, for example, monoaxial stretching in the machine direction can be performed by propelling the thermoplastic web over rolls of increasing speed. The most versatile stretching method that allows for monoaxial, sequential biaxial, and simultaneous biaxial stretching of a thermoplastic web employs a flat film tenter apparatus. Such an apparatus grasps the thermoplastic web using a plurality of clips, grippers, or other film edge-grasping means along opposing edges of the thermoplastic web in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Means such as diverging rails generally results in cross-direction stretching. Monoaxial and biaxial stretching can be accomplished, for example, by the methods and apparatus disclosed in U.S. Pat. No. 7,897,078 (Petersen et al.) and the references cited therein. Flat film tenter stretching apparatuses are commercially available, for example, from Brückner Maschinenbau GmbH, Siegsdorf, Germany.

In some embodiments, stretching is performed at elevated temperatures. This may allow the thermoplastic backing to be more flexible for stretching. Heating can be provided, for example, by IR irradiation, hot air treatment or by performing the stretching in a heat chamber. In some embodiments, heating is only applied to the second surface of the thermoplastic backing (i.e., the surface opposite the first surface from which the upstanding fastening elements project) to minimize any damage to the upstanding fastening elements that may result from heating. For example, in these embodiments, only rollers that are in contact with the second surface of the thermoplastic backing are heated.

The initial thickness (i.e., before stretching) of the thermoplastic backing may be up to about 250 μm or 150 μm and/or at least about 50 μm, 75 μm, or 100 μm, depending on the desired draw ratio and post-stretch thickness of the backing. In some embodiments, the initial thickness of the thermoplastic backing is in a range from 50 μm to about 225 μm, from about 75 μm to about 200 μm, or from about 75 μm to about 150 μm. After stretching, the thickness of the thermoplastic backing is decreased so that the ratio of the thickness of the thermoplastic backing before stretching to the thickness of the thermoplastic backing after stretching can be, for example, from 1.5:1 to 5:1, in some embodiments, from 1.5:1 to 3:1. The thickness of the thermoplastic backing after stretching is typically in a range from 20 μm to 80 μm and may be, in some embodiments, in a range from 20 μm to 70 μm or 30 μm to 70 μm.

In the embodiments where the mechanical fastener according to the present disclosure is stretched, the thermoplastic backing has stretch-induced molecular orientation in at least one direction. Whether a thermoplastic backing has stretch-induced molecular orientation can be determined by standard spectrographic analysis of the birefringent properties of the oriented thermoplastic polymer forming the backing. The mechanical fastener having stretch-induced molecular orientation may also be said to be birefringent, which means that the thermoplastic backing has different effective indexes of refraction in different directions. In the present application, whether the thermoplastic backing has stretch-induced molecular orientation is measured with a retardance imaging system available from Lot-Oriel GmbH & Co., Darmstadt, Germany, under the trade designation "LC-PolScope" on a microscope available from Leica Microsystems GmbH, Wetzlar, Germany, under the trade designation "DMRXE" and a digital CCD color camera available from QImaging, Surrey, BC, Canada, under the trade designation "RETIGA EXi FAST 1394". The microscope is equipped with a 546.5 nm interference filter obtained from Cambridge Research & Instrumentation, Inc., Hopkinton, Mass., and 10×/0.25 objective.

Advantageously, a variety of densities of the upstanding fastening elements may be useful for the mechanical fasteners according to the present disclosure. In some embodiments of the mechanical fastener according to the present disclosure, the upstanding fastening elements have a density of at least 248 per square centimeter ($cm^2$) (1600 per square inch, $in^2$) and up to about 1500/$cm^2$ (10000/$in^2$), 1240/$cm^2$ (8000/$in^2$), or 852/$cm^2$ (5500/$in^2$). In some embodiments, the density of the upstanding fastening elements may be in a range from 271/$cm^2$ (1750/$in^2$) to about 852/$cm^2$ (5500/$in^2$) or from 248/$cm^2$ (1600/$in^2$) to 542/$cm^2$ (3500/$in^2$). In some embodiments, the density of the upstanding fastening elements is about 465/$cm^2$ (3000/$in^2$). The spacing of the upstanding fastening elements need not be uniform.

In the embodiments wherein the thermoplastic backing is stretched, the initial density of the upstanding fastening elements before stretching may be at least 542/$cm^2$ (3500/$in^2$), 787/$cm^2$ (5000/$in^2$), or 852/$cm^2$ (5500/$in^2$) and may be up to 1550/$cm^2$ (10000/$in^2$). Stretching may then be carried out at the appropriate stretch ratio to achieve the desired density of upstanding fastening elements.

The density of the upstanding fastening elements and the cap area may be used to determine a relative cap density in the mechanical fastener disclosed herein. The relative cap density, which is sometimes referred to as an aspect ratio, can affect the feel of the mechanical fastener when the upstanding fastening elements come into contact with a person's skin. The relative cap density is a measurement of the aggregate cap area divided by the overall area of the mechanical fastener. In some embodiments of the mechanical fastener disclosed herein, relative cap density is in a range from 10 percent to 40 percent, and, in some embodiments, 10 percent to 30 percent, 15 percent to 30 percent, or 10 percent to 24 percent.

For any of the embodiments of the mechanical fastener according to the present disclosure, the thermoplastic backing may be in the form of a roll, from which mechanical fastener patches, for example, may be cut in a size appropriate to the desired application. In this application, the thermoplastic backing may also be a patch that has been cut to a desired size. In some of these embodiments, the second surface of the thermoplastic backing (i.e., the surface opposite the first surface from which the upstanding fastening elements project) may be coated with an adhesive (e.g., a pressure sensitive adhesive). In such embodiments, when the thermoplastic backing is in the form of a roll, a release liner may be applied to the exposed adhesive.

In some embodiments of the mechanical fastener disclosed herein, the thermoplastic backing is not joined to a carrier, at least when it is initially formed. In other embodiments, the second surface of the thermoplastic backing (i.e., the surface opposite the first surface from which the upstanding fastening elements project) is joined to a carrier. The thermoplastic backing may be joined to a carrier, for example, by lamination (e.g., extrusion lamination), adhesives (e.g., pressure sensitive adhesives), or other bonding methods (e.g., ultrasonic bonding, compression bonding, or surface bonding). The thermoplastic backing may also be joined to a carrier during the formation of the thermoplastic backing with upstanding posts. The resulting article may be a fastening laminate, for example, a fastening tab joined to the back sheet of an absorbent article useful for joining the front waist region and the rear waist region of an absorbent article.

The carrier, which in some embodiments may be joined to the second surface of the thermoplastic backing, may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multilayered films, coextruded films, or films comprising foam layers), and combinations thereof. In some embodiments, the carrier is a fibrous material (e.g., a woven, nonwoven, or knit material). The term "nonwoven" when referring to a carrier or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes. In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer.

Fibrous materials that provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

One or more zones of the carrier may comprise one or more elastically extensible materials extending in at least one direction when a force is applied and returning to approximately their original dimension after the force is removed. The term "elastic" refers to any material that exhibits recovery from stretching or deformation. Likewise, "nonelastic" materials, which do not exhibit recovery from stretching or deformation, may be useful for the carrier as well.

Mechanical fasteners according to the present disclosure are useful components in fastening systems that include the mechanical fastener according to any of the above embodiments and a loop material. Although mechanical fasteners according to the present disclosure are useful with a variety of different loop materials, in some embodiments, the loop material is a low-loft loop material, which is desirable for use in fastening systems because of their low cost and low material-usage. Examples of low-loft materials include nonwoven materials, for example, made from any of the materials described above for carriers. In some embodiments, the loop material has a fiber basis weight in a range from 10 grams per square meter (gsm) to 30 gsm. Fiber basis weight is a basis weight of just the fiber in the loop material (e.g., removed from any backing). In some embodiments, the loop material has a fiber basis weight in a range from 10 gsm to 20 gsm or from 15 gsm to 20 gsm. In some embodiments, the loop material has a fiber diameter in a range from 15 micrometers to 25.4 micrometers. The loop material may have a loop height of up to 500 µm and a loop width of up to 2500 µm. In some embodiments, the loop material has a fiber basis weight in a range from 20 grams per square meter to 30 grams per square meter, and the mechanical fastener engages with the loop material with a shear strength of at least 2000 gram-force. However, in other embodiments, mechanical fasteners may be useful with loop materials having fiber basis weights in a range from 30 gsm to 50 gsm as well.

The fastening laminate that can be formed after joining the thermoplastic backing to a carrier may be useful, for example, in disposable absorbent articles. Some examples of absorbent articles have at least a front waist region, a rear waist region, and a longitudinal center line bisecting the front waist region and the rear waist region, wherein at least one of the front waist region or the rear waist region comprises the structured surface made according to the method disclosed herein. The fastening laminate may be in the form of a fastening tab that is bonded to at least one of the front waist region or the rear waist region extending outwardly from at least one of the left longitudinal edge or the right longitudinal edge of the absorbent article. In other embodiments, the fastening laminate may be an integral ear portion of the absorbent article.

Figure 2:
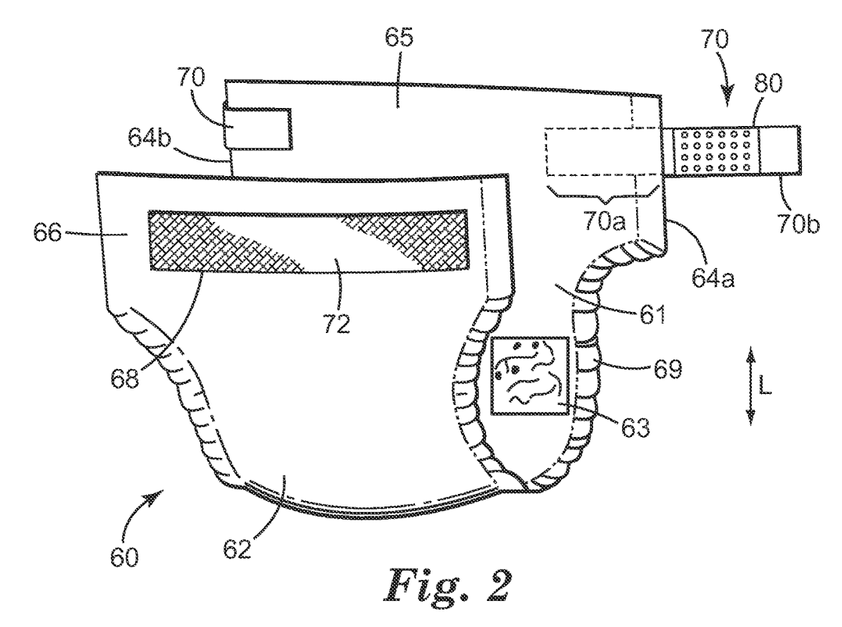
FIG. 2 is a perspective view of an exemplary disposable absorbent article that includes a mechanical fastener according to the present disclosure.

FIG. 2 is a schematic perspective view of an embodiment of an absorbent article according to the present disclosure. The absorbent article is a diaper 60 having an essentially hourglass shape. The diaper comprises an absorbent core 63 between a liquid permeable top sheet 61 that contacts the wearer's skin and an outwardly facing liquid impermeable back sheet 62. Diaper 60 has a rear waist region 65 having two fastening tabs 70 arranged at the two longitudinal edges 64a, 64b of diaper 60. The diaper 60 may comprise an elastic material 69 along at least a portion of longitudinal side edges 64a and 64b to provide leg cuffs. The longitudinal direction "L" of the absorbent article (e.g., diaper 60) refers to the direction that the article extends from the front to rear of the user. Therefore, the longitudinal direction refers to the length of the absorbent article between the rear waist region 65 and the front waist region 66. The lateral direction of the absorbent article (e.g., diaper 60) refers to the direction that the article extends from the left side to the right side (or vice versa) of the user (i.e., from longitudinal edge 64a to longitudinal edge 64b in the embodiment of FIG. 2).

In FIG. 2, fastening tabs 70 are secured through their manufacturer's end 70a to the rear waist region 65. The user's end 70b of the fastening tab comprises a mechanical fastener 80 according to the present disclosure. In some embodiments, when attaching the diaper 60 to a wearer's body, the user's ends 70b of fastening tabs 70 can be attached to a target area 68 comprising fibrous material 72 which may be arranged on the back sheet 62 of the front waist region 66. Examples of loop tapes which may be applied to the target area 68 to provide an exposed fibrous material 72, are disclosed, for example, in U.S. Pat. No. 5,389,416 (Mody et al.), EP 0,341,993 (Gorman et al.), and EP 0,539,504 (Becker et al.). In other embodiments, the back sheet 62 comprises a woven or nonwoven fibrous layer which is capable of interacting with the user's ends 70b of the fastening tabs 70 comprising a mechanical fastener disclosed herein. Examples of such back sheets 62 are disclosed, for example, in U.S. Pat. No. 6,190,758 (Stopper) and U.S. Pat. No. 6,075,179 (McCormack et al.) and described in the Examples, below. Advantageously, with the level of engagement possible with the mechanical fastener according to the present disclosure, good fastening between the hook strip 70 and the back sheet 62 may be possible, allowing the elimination of target area 68. Accordingly, in some embodiments, the disposable absorbent article disclosed herein is free of a target loop landing zone. In some embodiments, at least one of the front waist region or the rear waist region comprises a loop material having a fiber basis weight in a range from 10 gsm to 20 gsm.

Although the embodiment illustrated in FIG. 2 is an absorbent article with attached fastening tabs, it is envisioned that the mechanical fastener disclosed herein would be equally useful in absorbent articles with larger areas of hooks. For example, the ears of the absorbent article can themselves comprise the mechanical fastener disclosed herein, or the absorbent article can have two target zones of loop material along the longitudinal edges of the back sheet in one waist region and two hook strips extending along the longitudinal edges of the absorbent article in the opposite waist region.

Fastening laminates according to the present disclosure may also be useful, for example, as fastening tabs for pants-style diapers such as those described in U.S. Pat. No. 5,531,732 (Wood). In some embodiments, the absorbent article according to the present disclosure is a disposable pants-style diaper having a fibrous outer covering or back sheet that can engage with upstanding fastening elements on a fastening tab disclosed herein. The fastening tab can be located on a seam or side panel portion of the pants-style diaper such that a free end of the fastening tab is able to engage the fibrous outer covering or back sheet. The fastening tab free end is useful, for example, for adjusting the pants-style diaper's circumferential fit or size (in other words, waist fit or size) by gathering the side panel portion. The side panel portion may be free of any integrally bonded absorbent core structure in some embodiments. In some embodiments, the pants-style diaper has at least one perforation line extending from the waist opening to one of the leg openings. The perforation is generally near the side seam, may be positioned toward the front portion of the diaper, and may be parallel or non-parallel to the side seam. In some embodiments, the pants-style diaper has a pair of perforation lines, one on each side of the diaper. The perforation line(s) can either be broken before the diaper is positioned around the user's torso or while the user is wearing the diaper. The fastening tab free end can then be used to refasten the diaper so that it is snug around the user's waist. The fastening tab free end may also be useful, for example, as a disposal means when the pants-style diaper is removed from the wearer (e.g., by tearing the side panel or perforation line). The fastening tab typically remains on the side panel portion. The diaper can then be rolled into a compact form for disposal, and the fastening tab can be used to keep the diaper in a rolled form.

In some embodiments, a fastening tab according to the present disclosure can be applied to a pants-style diaper in a manufacturing process by using a laminate in which separated strips of the mechanical fastener disclosed herein are laminated to a nonwoven web using any of the methods described above. In some embodiments, two strips of the mechanical fastener can be positioned on the nonwoven web with the nonwoven extending beyond the mechanical fastener strips on both sides such that there are first and second side portions and a central portion of exposed nonwoven separated by the mechanical fastener strips of the laminate. The laminate can be in the form of a roll with longitudinally extending separated mechanical fastener strips. In an efficient embodiment of the manufacturing process of a pants-style diaper, the laminate can be cut in the cross-direction to a desired width of a fastening tab and aligned with two connected diapers in a web of diaper chassis. Then, the laminate can be cut down the middle of the central portion of exposed nonwoven at or about the same time the two connected diapers are cut apart so that half the laminate is applied to one diaper and half is applied to the other diaper. Then bonding of the side seams of the diaper and bonding of the fastening tab to the side seams can be carried out simultaneously, if desired. In these embodiments, each of the first and second side portions of exposed nonwoven can advantageously serve as a fingerlift for the left and right fastening tabs of two different pants-style diapers.

The fastening laminate including the mechanical fastener disclosed herein may also be useful, for example, for absorbent articles such as sanitary napkins. A sanitary napkin typically includes a back sheet that is intended to be placed adjacent to the wearer's undergarment. The back sheet may comprise a thermoplastic backing with spaced-apart, upstanding capped posts to securely attach the sanitary napkin to the undergarment, which mechanically engages with the capped posts. The back sheet may formed with upstanding capped posts. In other embodiments, the mechanical fastener may be in the form of a strip or patch that is attached to the back sheet with adhesive or using another bonding mechanism.

In other embodiments, the mechanical fastener according to the present disclosure may be useful, for example, in absorbent pads having at least a top sheet, an absorbent core, and a back sheet, wherein the back sheet comprises the mechanical fastener. The back sheet may formed with upstanding capped posts. In other embodiments, the mechanical fastener may be in the form of a strip or patch that is attached to the back sheet with adhesive or using another bonding mechanism. The absorbent pads may be useful, for example, in adult incontinence articles, which may be in the form of an open-type diaper having the general shape such as that shown in FIG. 2 or a pants-type diaper. In these embodiments, the mechanical fastener is useful for affixing the absorbent pad to the top sheet of the adult incontinence article, and adequate shear is useful for holding the pad in place while the peel strength of the mechanical fastener should be low enough so that the pad may be easily removed by the user or the caregiver. In other embodiments, absorbent pads including the mechanical fastener according to the present disclosure may be attached directly to a user's undergarments for the purpose of urine absorption. It has been conventionally thought that increasing hook density and increasing hook height may be useful for increasing engagement with a loop material (see, e.g., Int. Pat. Appl. Pub. No. WO 2006/101844 (Petersen et al.), and such changes tend to increase the basis weight of mechanical fastening members. It has now been found that mechanical fasteners according to the present disclosure provide surprisingly high shear and peel performance against low-loft loop materials despite their low basis weights. As shown in the Examples below, the mechanical fasteners according to the present disclosure provide engagement to loop materials that is comparable to or exceeds that of commercially available hook fasteners designed to engage with low-loft loop materials.

The low basis weight of the mechanical fastener disclosed herein provides the advantages that the fastener is flexible, which lessens the tendency for the mechanical fastener to become disengaged when the mechanical fastening members are twisted. The mechanical fasteners disclosed herein are typically soft (e.g., may have a cloth-like feeling) and may be less irritating to a user's skin (e.g., when the mechanical fastener is on an absorbent article) because of their low basis weight and typically low thickness. And the mechanical fasteners disclosed herein require less material and are therefore less expensive to manufacture.

A comparison of the softness of the mechanical fastener according to the present disclosure and an example mechanical fastener having a higher basis weight is shown in Examples 29 and Illustrative Example 6, below. The mechanical fastener according to the present disclosure as measured by loop softness was significantly less than a mechanical fastener having a higher base film thickness and capped post height.

Unexpectedly, the mechanical fastener according to some embodiments of the present disclosure has increased shear performance, relative to a comparable mechanical fastener having the same dimensions but with a thicker thermoplastic backing and a higher density of fastening elements. For example, a comparison of Illustrative Example 4 and Example 3 and a comparison of Illustrative Example 5 and Example 4 in the following Examples show that shear performance is unexpectedly improved upon stretching the thermoplastic backing and decreasing its thickness even though the density of the upstanding elements is reduced by half.

The mechanical fasteners according to the present disclosure provide useful shear strength for pad fixation of adult incontinence applications. As shown in the Examples, below, for example, Examples 20 to 28, there is a tendency for peel strength toward a nonwoven top sheet material to decrease as the size of the cap diameter and cap overhang decrease. In some embodiments, in a mechanical fastener useful for pad fixation, the thermoplastic backing has a thickness in a range from 40 µm to 75 µm, and the upstanding fastening elements have a height in a range from 50 µm to 300 µm (in some embodiments, 100 µm to 300 µm or 150 µm to 300 µm), a cap diameter in a range from 190 µm to 320 µm (in some embodiments, 200 µm to 300 µm), and a cap overhang from in a range from 5 µm to 65 µm. For open-style adult incontinence articles, the cap overhang may be in a range from 5 µm to 30 µm (in some embodiments, 10 µm to 30 µm or 15 µm to 25 µm) and for pants-style adult incontinence articles, the cap overhang may be in a range from 30 µm to 65 µm (in some embodiments, 30 µm to 55 µm or 30 µm to 50 µm). For adult incontinence applications, an open-style diaper may be applied by a caregiver on a user who may be bedridden. In these applications, the peel strength of the mechanical fastener to hold the absorbent pad on the top sheet of the diaper may be lower than the peel strength needed for a pants-style diaper. Therefore, a lower cap overhang may be useful, for example, as in Example 23, below. A pants-style diaper may be taken on and off independently by a user, who is typically more active than a user of an open-style diaper. Because of this increased motion, a higher peel strength between the absorbent pad and the diaper, and consequently a larger cap overhang, may be useful for pants-style diapers.

Some Embodiments of the Disclosure

In a first embodiment, the present disclosure provides mechanical fastener comprising:

a thermoplastic backing; and multiple, upstanding fastening elements that have a post with a proximal end attached to the thermoplastic backing and a distal end comprising a cap larger in area than a cross-sectional area of the post, wherein the multiple, upstanding fastening elements have a height up to 300 micrometers, and wherein the basis weight of the mechanical fastener is in a range from 25 grams per square meter to 75 grams per square meter.

In a second embodiment, the present disclosure provides a mechanical fastener according to the first embodiment, wherein the cap extends beyond the post on at least two opposing sides of the post.

In a third embodiment, the present disclosure provides a mechanical fastener according to the first or second embodiment, wherein the height of the upstanding fastening elements is at least 100 micrometers.

In a fourth embodiment, the present disclosure provides a mechanical fastener according to any one of the first to third embodiments, wherein the thermoplastic backing has a thickness in a range from 20 micrometers to 80 micrometers.

In a fifth embodiment, the present disclosure provides a mechanical fastener according to the any one of the first to fourth embodiments, wherein the cap extends an overhang distance beyond the post, and wherein the overhang distance is in a range from 5 micrometers to 85 micrometers.

In a sixth embodiment, the present disclosure provides a mechanical fastener according to any one of the first to fifth embodiments, wherein a quotient of the overhang distance divided by the height is up to 0.6.

In a seventh embodiment, the present disclosure provides a mechanical fastener according to any one of the first to sixth embodiments, wherein at least a portion of the post decreases in size from the proximal end to the distal end.

In an eighth embodiment, the present disclosure provides a mechanical fastener according to any one of the first to seventh embodiments, wherein at least a portion of the overhang is turned down toward the thermoplastic backing.

In a ninth embodiment, the present disclosure provides a mechanical fastener according to any one of the first to eighth embodiments, wherein upstanding fastening elements are present on the thermoplastic backing in a density range from 248 per square centimeter to 542 per square centimeter.

In a tenth embodiment, the present disclosure provides a fastening system according to any one of the first to ninth embodiments, wherein the thermoplastic backing has stretch-induced molecular orientation in at least one direction.

In an eleventh embodiment, the present disclosure provides a fastening system according to any one of the first to tenth embodiments, wherein the upstanding fastening elements have a height up to 285 micrometers.

In a twelfth embodiment, the present disclosure provides a fastening system comprising a mechanical fastener according to any one of the first to eleventh embodiments and a loop material for engaging with the mechanical fastener.

In a thirteenth embodiment, the present disclosure provides a fastening system according to the twelfth embodiment, wherein the loop material is has a fiber basis weight in a range from 10 grams per square meter to 30 grams per square meter.

In a fourteenth embodiment, the present disclosure provides a fastening system according to the twelfth embodiment, wherein the loop material has a fiber basis weight in a range from 20 grams per square meter to 30 grams per square meter, and wherein the mechanical fastener engages with the loop material with a shear strength of at least 2000 gram-force.

In a fifteenth embodiment, the present disclosure provides a fastening system according to any one of the twelfth to fourteenth embodiments, wherein the loop material has a fiber diameter in a range from 15 micrometers to 25 micrometers.

In a sixteenth embodiment, the present disclosure provides an absorbent article comprising the mechanical fastener according to any one of the first to eleventh embodiments.

In a seventeenth embodiment, the present disclosure provides an absorbent article according to the sixteenth embodiment, further comprising a front waist region and a rear waist region, wherein at least one of the front waist region or the rear waist region comprises the mechanical fastener.

In an eighteenth embodiment, the present disclosure provides the absorbent article according to the seventeenth embodiment, wherein the front waist region comprises a loop material having a fiber basis weight in a range from 10 grams per square meter to 20 grams per square meter.

In a nineteenth embodiment, the present disclosure provides the absorbent article according to the sixteenth embodiment, wherein the absorbent article is an absorbent pad having at least a top sheet, an absorbent core, and a back sheet, wherein the back sheet comprises the mechanical fastener according to any one of the first to eleventh embodiments.

In a twentieth embodiment, the present disclosure provides the absorbent article according to the nineteenth embodiment, wherein the absorbent pad is attached to a top sheet of a diaper or attached to an undergarment.

In a twenty-first embodiment, the present disclosure provides the absorbent article according to the nineteenth or twentieth embodiment, wherein the thermoplastic backing has a thickness in a range from 40 micrometers to 75 micrometers, and wherein the upstanding fastening elements have a height in a range from 150 micrometers to 300 micrometers, a cap diameter in a range from 190 micrometers to 320 micrometers, and a cap overhang from in a range from 5 micrometers to 65 micrometers.

In a twenty-second embodiment, the present disclosure provides the absorbent article according to the sixteenth embodiment, wherein the absorbent article is a pants-style diaper, and wherein the mechanical fastener is located on a tab on a seam or side panel portion of the pants-style diaper.

In a twenty-third embodiment, the present disclosure provides the mechanical fastener according to any one of the first to eleventh embodiments, wherein the upstanding fastening elements do not have the combination of all the following dimensions: a cap thickness of 48 micrometers, a cap diameter in the cross-direction of 260 micrometers, a cap diameter in the machine direction of 196 micrometers, a backing thickness of 50 micrometers, a height of 169 micrometers, a post diameter at the base of 157 micrometers, and a post diameter below the cap of 145 micrometers.

In order that this disclosure can be more fully understood, the following examples are set forth. It should be understood that these examples are for illustrative purposes only, and are not to be construed as limiting this disclosure in any manner.

EXAMPLES

Mechanical Fastener Strips

The mechanical fastener strips of Examples 1-19, Comparative Example 1 (part number CHK-01324 available from the 3M Company, St. Paul, Minn.), and Illustrative Examples 1-5 were prepared from an ethylene-propylene copolymer available from Dow Chemical Company, Midland, Mich., under the trade designation "C700-35N" using the method described in U.S. Pat. No. 5,845,375 (Miller et al.). The mechanical fastener strips of Examples 1-19 were arranged in square or staggered arrays and had densities of the upstanding fastening elements that ranged from 271-542 per square centimeter. The mechanical fastener strips with densities of 271/cm² were prepared by machine stretching of corresponding 542/cm² strips in the machine direction with a draw ratio of 2:1. Examples 3 and 4 were prepared by stretching Illustrative Examples 4 and 5, respectively, in the machine direction with a draw ratio of 2:1. The posts were either conical or rectangular in shape. Upstanding fastening elements with "grooved caps" were prepared according to the process described in U.S. Pat. No. 5,868,987 (Kampfer et al.). The term "bumped" describes caps that were reshaped so that the overhanging portions of the distal cap, that extend beyond the post, were pushed down toward the backing (process for reshaping described in U.S. Pat. No. 6,132,660 (Kampfer)).

The mechanical fastener strip of Comparative Example 1 is also available by removing the hook tab from the commercially available adult diaper "TENA ULTRA" (SCA Corporation, Stockholm, Sweden). The hook strip of Comparative Example 2 was obtained by removing the hook tab from the commercially available adult diaper "PREVAIL BREEZERS" (First Quality Corporation, Great Neck, N.Y.).

In Table 1, the density of the upstanding fastening elements (in number per square centimeter), cap shape (round or oval), cap shape (bumped or unbumped), and cap appearance (grooved or smooth) are recorded for the mechanical fastener strips of Examples 1-19, Comparative Examples (Comp. Ex.) 1-2, and Illustrative Examples (Illustrative Ex.) 1-5.

TABLE 1

| Example | Density (number/cm²) | Cap Shape (round or oval) | Bumped Cap | Grooved Cap |
|---|---|---|---|---|
| Example 1 | 542 | oval | no | yes |
| Example 2 | 542 | oval | yes | yes |
| Example 3 | 271 | oval | yes | yes |
| Example 4 | 271 | oval | yes | yes |
| Example 5 | 542 | oval | no | yes |
| Example 6 | 542 | oval | yes | yes |
| Example 7 | 271 | round | yes | no |
| Example 8 | 542 | oval | no | yes |
| Example 9 | 542 | oval | yes | yes |
| Example 10 | 542 | round | no | no |
| Example 11 | 542 | round | yes | no |
| Example 12 | 271 | round | yes | no |
| Example 13 | 542 | round | no | no |
| Example 14 | 542 | round | yes | no |
| Example 15 | 542 | round | yes | no |
| Example 16 | 542 | round | no | no |
| Example 17 | 542 | round | yes | no |
| Example 18 | 542 | oval | no | yes |
| Example 19 | 542 | oval | yes | yes |
| Comp. Ex. 1 | 248 | oval | no | yes |
| Comp. Ex. 2 | 294 | round | no | no |
| Illustrative Ex. 1 | 271 | oval | yes | yes |
| Illustrative Ex. 2 | 271 | oval | yes | yes |
| Illustrative Ex. 3 | 248 | oval | yes | yes |
| Illustrative Ex. 4 | 542 | oval | yes | yes |
| Illustrative Ex. 5 | 542 | oval | yes | yes |

In Table 2, measured values of cap thickness, cap diameter in the cross-direction (CD), and cap diameter in the machine direction (MD) are recorded for the mechanical fastener strips of Examples 1-19, Comparative Examples 1-2, and Illustrative Examples 1-5.

TABLE 2

| Example | Cap Thickness (μm) | Cap Diameter in CD (μm) | Cap Diameter in MD (μm) |
|---|---|---|---|
| Example 1 | 47 | 300 | 200 |
| Example 2 | 48 | 330 | 201 |
| Example 3 | 50 | 291 | 198 |
| Example 4 | 53 | 329 | 228 |
| Example 5 | 31 | 187 | 167 |
| Example 6 | 31 | 207 | 167 |
| Example 7 | 60 | 306 | 318 |
| Example 8 | 48 | 272 | 196 |
| Example 9 | 48 | 260 | 196 |
| Example 10 | 19 | 164 | 180 |
| Example 11 | 19 | 157 | 180 |
| Example 12 | 64 | 309 | 342 |
| Example 13 | 35 | 197 | 225 |
| Example 14 | 35 | 197 | 225 |
| Example 15 | 32 | 216 | 225 |
| Example 16 | 47 | 269 | 253 |
| Example 17 | 47 | 261 | 253 |
| Example 18 | 57 | 291 | 200 |
| Example 19 | 57 | 304 | 200 |
| Comparative Example 1 | 55 | 350 | 226 |
| Comparative Example 2 | 35 | 364 | 364 |
| Illustrative Example 1 | 50 | 310 | 194 |
| Illustrative Example 2 | 53 | 340 | 218 |
| Illustrative Example 3 | 65 | 350 | 220 |
| Illustrative Example 4 | 57 | 309 | 198 |
| Illustrative Example 5 | 54 | 329 | 228 |

In Table 3, measured values of the backing thickness, post height prior to capping, capped post height, post diameter measured at the base (distance "w" in FIG. 1), post diameter measured immediately below the cap (distance "w¹" in FIG. 1), and basis weight are recorded for the mechanical fastener strips of Examples 1-19, Comparative Examples 1-2, and Illustrative Examples 1-5. The capped post height is defined as the distance measured from the top surface of the backing to the tip of the cap (distance "h" in FIG. 1).

TABLE 3

| Example | Backing Thickness (μm) | Post Height Prior to Capping (μm) | Capped Post Height (μm) | Post Diameter at Base (μm) | Post Diameter below Cap (μm) | Basis Weight (gsm) |
|---|---|---|---|---|---|---|
| Example 1 | 46 | 350 | 247 | 188 | 178 | 50 |
| Example 2 | 50 | 350 | 219 | 171 | 181 | 55 |
| Example 3 | 50 | 350 | 193 | 170 | 163 | 65 |
| Example 4 | 50 | 350 | 159 | 170 | 165 | 65 |
| Example 5 | 50 | 250 | 189 | 149 | 130 | 55 |
| Example 6 | 50 | 250 | 183 | 146 | 132 | 55 |
| Example 7 | 50 | 350 | 176 | 169 | 163 | 65 |
| Example 8 | 50 | 250 | 169 | 158 | 152 | 55 |
| Example 9 | 50 | 250 | 169 | 157 | 145 | 55 |
| Example 10 | 50 | 250 | 187 | 147 | 138 | 55 |
| Example 11 | 50 | 250 | 203 | 147 | 138 | 56 |
| Example 12 | 50 | 350 | 159 | 171 | 170 | 70 |
| Example 13 | 50 | 250 | 161 | 150 | 140 | 55 |
| Example 14 | 50 | 250 | 161 | 150 | 140 | 55 |
| Example 15 | 53 | 250 | 147 | 141 | 137 | 55 |
| Example 16 | 50 | 250 | 125 | 154 | 153 | 55 |
| Example 17 | 50 | 250 | 117 | 150 | 144 | 55 |
| Example 18 | 50 | 250 | 135 | 159 | 159 | 55 |
| Example 19 | 50 | 250 | 130 | 151 | 151 | 55 |
| Comparative Example 1 | 100 | 440 | 386 | 240 | 196 | 105 |
| Comparative Example 2 | 100 | not available | 184 | 371 | 209 | 102 |
| Illustrative Example 1 | 50 | 440 | 350 | 170 | 147 | 72 |
| Illustrative Example 2 | 50 | 440 | 330 | 170 | 155 | 72 |

TABLE 3-continued

| Example | Backing Thickness (μm) | Post Height Prior to Capping (μm) | Capped Post Height (μm) | Post Diameter at Base (μm) | Post Diameter below Cap (μm) | Basis Weight (gsm) |
|---|---|---|---|---|---|---|
| Example 2 | | | | | | |
| Illustrative Example 3 | 100 | 350 | 275 | 240 | 198 | 110 |
| Illustrative Example 4 | 92 | 350 | 239 | 161 | 159 | 100 |
| Illustrative Example 5 | 91 | 350 | 230 | 179 | 173 | 95 |

In Table 4, the calculated cap overhang, bending index (BI), and relative cap density values are recorded for Examples 1-19, Comparative Examples 1-2, and Illustrative Examples 1-5. The cap overhang was calculated using the following equation:

Cap Overhang(μm)=(Cap Diameter−Post Diameter Below Cap)/2

The bending index (BI) was calculated using the following equation:

BI=Cap Overhang/Capped Post Height.

For the equation, the cap diameter was measured in the longest dimension and the post diameter was measured just below the cap.

The relative cap density was calculated using the following equation:

Relative Cap Density=aggregate cap area/area of the mechanical fastener.

TABLE 4

| Example | Cap Overhang (calculated) (μm) | Bending Index (calculated) | Relative Cap Area (calculated) |
|---|---|---|---|
| Example 1 | 61 | 0.25 | 25.5% |
| Example 2 | 75 | 0.34 | 28.2% |
| Example 3 | 64 | 0.33 | 12.3% |
| Example 4 | 82 | 0.52 | 16.0% |
| Example 5 | 29 | 0.15 | 13.3% |
| Example 6 | 38 | 0.21 | 14.7% |
| Example 7 | 72 | 0.41 | 20.7% |
| Example 8 | 60 | 0.36 | 22.7% |
| Example 9 | 58 | 0.34 | 21.7% |
| Example 10 | 13 | 0.07 | 12.6% |
| Example 11 | 10 | 0.05 | 12.0% |
| Example 12 | 70 | 0.44 | 22.5% |
| Example 13 | 29 | 0.18 | 18.9% |
| Example 14 | 29 | 0.18 | 18.9% |
| Example 15 | 40 | 0.27 | 20.7% |
| Example 16 | 58 | 0.46 | 29.0% |
| Example 17 | 59 | 0.50 | 28.1% |
| Example 18 | 66 | 0.49 | 24.8% |
| Example 19 | 77 | 0.59 | 25.9% |
| Comparative Example 1 | 71 | 0.20 | 15.4% |
| Comparative Example 2 | 77 | 0.42 | 30.6% |
| Illustrative Example 1 | 80 | 0.23 | 12.8% |
| Illustrative Example 2 | 95 | 0.29 | 15.8% |
| Illustrative Example 3 | 78 | 0.28 | 15.0% |
| Illustrative Example 4 | 74 | 0.31 | 26.0% |
| Illustrative Example 5 | 75 | 0.33 | 31.9% |

All recorded measurements in Tables 1-5 were taken using a Keyence VHX-600E microscope equipped with a VH-Z20R lens, a magnification range of 20× to 200×, and a data acquisition software package (Keyence Corporation, Osaka, Japan).

Test Method and Test Results

The disengagement performance characteristics of the mechanical fastener strips of Examples 1-19, Comparative Examples 1-2, and Illustrative Examples 1-5 were determined using tests for shear strength and peel strength. All testing was conducted at constant temperature (23° C.±2° C.) and relative humidity (50%±5%). All materials and equipment were equilibrated at these conditions for a minimum of 24 hours prior to testing. A universal constant rate of extension tensile testing instrument equipped with a computer for data recording and the required load ranges was used (Series 4200, 4500, or 5500 available from Instron Engineering Corporation, Canton, Mass.). The instrument crosshead speed was set to 305 mm/minute with a peel distance of at least 32 mm for all tests.

The mechanical fastener strips of Examples 1-19, Comparative Examples 1-2, and Illustrative Examples 1-5 were evaluated using three different polypropylene nonwoven loop samples. Sample 1 was a low-loft nonwoven loop material obtained from the backsheet of an adult diaper commercially available from First Quality Corporation, Great Neck, N.Y., under the trade designation "PREVAIL BREEZERS". Sample 2 was a low-loft nonwoven loop material obtained from the backsheet of an adult diaper commercially available from the SCA Corporation, Stockholm, Sweden, under the trade designation "TENA ULTRA". Sample 3 was a low-loft nonwoven loop material obtained from the backsheet of an adult diaper commercially available from Medline Industries, Mundelein, Ill., under the trade designation "RESTORE". In all tests, the outer surface (garment facing side) of the diaper backsheet was used for engagement with the mechanical fastener samples. In Table 5, measured values of the fiber diameter, loop height (loft), loop width, and fiber basis weight are recorded for nonwoven loop Samples 1-3.

TABLE 5

Dimensions for Nonwoven Samples 1-3

| Sample Number | Fiber Diameter (μm) | Loop Height (μm) | Loop Width (μm) | Fiber Basis Weight (gsm) |
|---|---|---|---|---|
| Sample 1 | 19 | 490 | 2450 | 25 |
| Sample 2 | 20 | 390 | 550 | 16 |
| Sample 3 | 20 | 360 | 900 | 14 |

In Test Method 1, the shear strength of fasteners prepared from the mechanical fastener strips of Examples 1-19, Comparative Examples 1-2, and Illustrative Examples 1-5 with the nonwoven loop materials of Samples 1-3 was measured according to ASTM D5169-98. The finished mechanical fastener test specimen was prepared as a 12.7 mm cross direction (CD) by 25.4 mm machine direction (MD) strip attached to a 76 mm by 25.4 mm leader of 898 filament tape (available from 3M Company, St. Paul, Minn.). An additional 76 mm by 25.4 mm strip of filament tape was used to cover the exposed adhesive (any remainder was folded over the first strip).

The finished nonwoven loop material was cut to form a 76 mm CD by 30 mm MD strip that was backed with a 76 mm by 30 mm strip of 898 filament tape. The Example mechanical fastener sample was gently placed with the fastening elements side down onto the corresponding loop face and secured with five cycles (five forward and five backward passes) of a 5 kilogram hand held roller. The materials were oriented so that the measurement of shear strength was conducted in the Example specimen CD and the loop CD. The leader of the Example specimen was attached to the upper jaw while the loop sample was attached to the lower jaw of the Instron instrument, allowing for a slight amount of slack.

The initial jaw separation (gauge length) was set to 76 mm. The instrument was started and the upper jaw traveled until the Example specimen was completely disengaged from the loop sample. Measurements were taken of the maximum load in units of gram-force (gf). The data collected from a minimum of ten replicates, each using fresh materials, was averaged and the averaged data is reported in Table 6.

TABLE 6

Shear Strength with Samples 1-3 as the Nonwoven Loop Material

| | Maximum Load (gf) | | |
|---|---|---|---|
| Example | Sample 1 | Sample 2 | Sample 3 |
| Example 1 | 1637 | 834 | 667 |
| Example 2 | 1199 | 827 | 560 |
| Example 3 | 2120 | 1445 | 1003 |
| Example 4 | 1377 | 936 | 631 |
| Example 5 | 3027 | 1544 | 1227 |
| Example 6 | 2823 | 1554 | 1168 |
| Example 7 | 2006 | 1333 | 1165 |
| Example 8 | 2080 | 1398 | 1129 |
| Example 9 | 1587 | 1042 | 582 |
| Example 10 | 3037 | 1644 | 1700 |
| Example 11 | 2907 | 1457 | 1761 |
| Example 12 | 1729 | 1227 | 531 |
| Example 13 | 3242 | 1432 | 1058 |
| Example 14 | 2431 | 1467 | 1087 |
| Example 15 | 2407 | 1235 | 863 |
| Example 16 | 1888 | 1261 | 809 |
| Example 17 | 1681 | 1212 | 721 |
| Example 18 | 945 | 1094 | 730 |
| Example 19 | 1430 | 587 | 344 |
| Comparative Example 1 | 1483 | 963 | 703 |
| Comparative Example 2 | 1818 | 765 | 653 |
| Illustrative Example 1 | 1904 | 1063 | 595 |
| Illustrative Example 2 | 1602 | 818 | 789 |
| Illustrative Example 3 | 1476 | 945 | 380 |
| Illustrative Example 4 | 1373 | 858 | 445 |
| Illustrative Example 5 | 928 | 839 | 588 |

In Test Method 2, the force required to peel the Example mechanical fasteners from the loop material at a 135 degree peel angle was measured. The test jig in the Instron tensile tester was set at 135 degrees (stationary). The finished mechanical fastener (selected from Examples 1-19, Comparative Examples 1-2, and Illustrative Examples 1-5) was prepared as a 19 mm CD by 25.4 mm MD strip with fastening tape used as the backing material. The finished Example specimen was attached to one end of a 25.4 mm by 203 mm paper leader. The finished nonwoven loop material (selected from Samples 1-3) was attached with double sided tape to a 51 mm by 127 mm by 1.6 mm steel plate. The Example specimen was gently placed with the fastening elements side down onto the corresponding loop face on the plate and secured with one cycle (one cycle=one forward and one backward pass) of a 2 kilogram hand held roller. The materials were oriented so that the peel was conducted in the Example specimen CD and the loop CD.

TABLE 7

Peel Strength with Samples 1-3 as the Nonwoven Loop Material

| | Maximum Load (gf) | | |
|---|---|---|---|
| Example | Sample 1 | Sample 2 | Sample 3 |
| Example 1 | 63 | 160 | 120 |
| Example 2 | 73 | 100 | 133 |
| Example 3 | 145 | 146 | 145 |
| Example 4 | 137 | 126 | 137 |
| Example 5 | 93 | 68 | 59 |
| Example 6 | 126 | 86 | 126 |
| Example 7 | 169 | 120 | 169 |
| Example 8 | 120 | 86 | 91 |
| Example 9 | 145 | 104 | 145 |
| Example 10 | 90 | 70 | 90 |
| Example 11 | 58 | 64 | 40 |
| Example 12 | 87 | 120 | 90 |
| Example 13 | 183 | 120 | 53 |
| Example 14 | 133 | 126 | 133 |
| Example 15 | 90 | 117 | 157 |
| Example 16 | 125 | 81 | 55 |
| Example 17 | 154 | 120 | 155 |
| Example 18 | 109 | 116 | 78 |
| Example 19 | 92 | 58 | 92 |
| Comparative Example 1 | 108 | 134 | 90 |
| Comparative Example 2 | 94 | 116 | 112 |
| Illustrative Example 1 | 100 | 130 | 84 |
| Illustrative Example 2 | 105 | 186 | 143 |
| Illustrative Example 3 | 131 | 95 | 111 |
| Illustrative Example 4 | 97 | 61 | 66 |
| Illustrative Example 5 | 108 | 95 | 97 |

The plate was placed into the 135 degree stationary jig on the Instron instrument and the paper lead was attached to the upper jaw of the instrument allowing for a slight amount of slack. The initial jaw separation (gauge length) was set to at least 203 mm. The instrument was started and measurements were taken of the maximum load (go. The data collected from a minimum of ten replicates, each using fresh materials, was averaged and the averaged data is reported in Table 7, above.

The mechanical fastening strips of Examples 20 to 28 were prepared according to the method described in Examples 1 to 19. The backings were not stretched. For each of Examples 20 to 28, the density of the upstanding fastening elements was 248/cm$^2$, and the basis weight was 62 grams per square meter. The post height before capping was 250 micrometers. The caps of Examples 20 to 28 were "grooved" according to the process described in U.S. Pat. No. 5,868,987 (Kampfer et al.). For Examples 25 to 28, the caps were also bumped according to the process described in U.S. Pat. No. 6,132,660 (Kampfer). Other characteristics of the Examples are shown in Table 8. The recorded measurements in Table 8, below, were taken at 175× magnification using a Keyence Corporation Keyence VHX-1000 microscope equipped with a data acquisition software package, a digital range finder, and a monitor.

The mechanical fastener strips of Examples 20 to 28 were evaluated using a spunbonded polypropylene nonwoven obtained from Mitsui Chemicals, Inc., Tokyo, Japan, under the trade designation "SYNTEX PS-104". For peel evaluation, a patch of the mechanical fastener (25 mm in the machine direction (MD) and 20 mm in the cross-direction (CD)) was attached to one end of a paper leader. The nonwoven material (50 mm in the MD and 100 mm in the CD) was attached with double sided tape to a metal plate. The mechanical fastener specimen was pressed onto the nonwoven using one cycle (one cycle=one forward and one backward pass) with a 100-gram roller. The materials were oriented so that the peel was conducted in the Example specimen CD and the nonwoven CD. The 90 degree peel was measured using an instrument obtained from Orientec Co., Ltd. (Fukaya, Japan), under the trade designation "TENSILON RTG-1225". The initial jaw gap was 150 mm, and a 300 mm per minute separation speed was used. The evaluation was repeated six times, and the average peel force was recorded. The results are shown in Table 8, below.

For shear performance evaluation, a patch of the mechanical fastener (25 mm in MD and 20 mm in the CD) was attached to one end of a paper leader. The nonwoven material (100 mm in the MD and 50 mm in the CD) was attached with double sided tape to a metal plate. The mechanical fastener specimen was pressed onto the nonwoven using one cycle (one cycle=one forward and one backward pass) with a 100-gram roller. The materials were oriented so that the measurement was conducted in the Example specimen CD and the nonwoven MD, and the paper leader extended beyond the edge of the nonwoven and metal plate. A ten-gram weight was placed on top of the Example specimen, and a 100-gram weight was attached to the paper leader. If the Example specimen did not move within ten seconds, an additional 100-gram weight was attached to the paper leader. This process was repeated until the Example specimen began to move within ten seconds after adding the weight. The amount of weight added before the Example specimen began to move was recorded. The evaluation was repeated three times, and the average was recorded and reported as shear force. The results are shown in Table 8, below.

Example 29 and Illustrative Example 6 were prepared according to the method of Examples 1 to 19. Example 29 had a density of the upstanding fastening elements of 3000/in$^2$ (465/cm$^2$), a backing thickness of 50 µm, a cap diameter in the CD of 350 µm, and a capped post height of 140 µm. Illustrative Example 6 had a density of the upstanding fastening elements of 900/in$^2$ (140/cm$^2$), a backing thickness of 110 µm, a cap diameter in the CD of 520 µm, and a capped post height of 550 µm. Loop stiffness was measured for each of these samples using the following method. A specimen was prepared by cutting the mechanical fastener of Example 29 or Illustrative Example 6 to a strip 10 mm long in the CD and 150 mm long in the MD. The specimen was placed on a sample holder so that the ends of the strip were flat against the sample holder, and a loop with a circumference of 54 mm was made with the center portion of the strip. The specimen was compressed to a height of 6.5 mm with a compression plate moving at 3.5 mm per second. The peak force was recorded and found to be 2.5 g/mm for Example 29 and 16.5 g/mm for Illustrative Example 6.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein. All patents and patent applications cited above are hereby incorporated by reference into this document in their entirety.

What is claimed is:

1. A mechanical fastener comprising:
a thermoplastic backing; and
multiple, upstanding fastening elements that have a post with a proximal end attached to the thermoplastic backing and a distal end comprising a cap larger in area than a cross-sectional area of the post,
wherein the multiple, upstanding fastening elements have a height of at least 40 micrometers and up to 300 micrometers, and wherein a basis weight of the mechanical fastener is in a range from 25 grams per square meter to 75 grams per square meter.

2. The mechanical fastener of claim 1, wherein the upstanding fastening elements have a height up to 285 micrometers.

3. The mechanical fastener of claim 1, wherein the cap extends beyond the post on at least two opposing sides of the post.

4. The mechanical fastener of claim 1, wherein the height of the upstanding fastening elements is at least 100 micrometers.

5. The mechanical fastener of claim 1, wherein the thermoplastic backing has a thickness in a range from 20 micrometers to 80 micrometers.

6. The mechanical fastener of claim 1, wherein the cap extends an overhang distance beyond the post, and wherein the overhang distance is in a range from 5 micrometers to 85 micrometers.

7. The mechanical fastener of claim 1, wherein the cap extends an overhang distance beyond the post, and wherein a quotient of the overhang distance divided by the height is up to 0.6.

8. The mechanical fastener of claim 1, wherein the upstanding fastening elements are present on the thermoplastic backing in a density range from 248 per square centimeter to 542 per square centimeter.

9. The mechanical fastener of claim 1, wherein the thermoplastic backing has stretch-induced molecular orientation in at least one direction.

TABLE 8

| Ex. | Cap Thickness (µm) | Cap Diameter in CD (µm) | Cap Diameter in MD (µm) | Backing Thickness (µm) | Capped Post Height (µm) | Post Diameter at Base (µm) | Post Diameter below Cap (µm) | Cap Overhang (calculated) (µm) | Bending Index (calculated) | Relative Cap Area (calculated) | 90 degree peel force (N/25 mm) | Shear force (g/500 mm$^2$) |
|---|---|---|---|---|---|---|---|---|---|---|---|---|
| 20 | 52 | 337 | 263 | 69 | 205 | 222 | 187 | 75 | 0.37 | 17.3 | 0.050 | 900 |
| 21 | 50 | 370 | 281 | 59 | 176 | 227 | 195 | 88 | 0.50 | 20.3 | 0.076 | 566 |
| 22 | 65 | 414 | 306 | 58 | 167 | 224 | 204 | 105 | 0.63 | 24.7 | 0.059 | 700 |
| 23 | 33 | 210 | 205 | 56 | 249 | 229 | 172 | 19 | 0.08 | 8.39 | 0.0092 | 1166 |
| 24 | 46 | 313 | 244 | 58 | 210 | 226 | 188 | 63 | 0.30 | 14.9 | 0.109 | 766 |
| 25 | 47 | 250 | 230 | 52 | 241 | 238 | 189 | 31 | 0.13 | 11.20 | 0.0517 | 733 |
| 26 | 52 | 296 | 250 | 49 | 216 | 237 | 196 | 50 | 0.23 | 14.41 | 0.0695 | 600 |
| 27 | 53 | 287 | 254 | 57 | 201 | 226 | 185 | 51 | 0.25 | 14.20 | 0.0938 | 500 |
| 28 | 50 | 293 | 254 | 54 | 214 | 229 | 198 | 48 | 0.22 | 14.50 | 0.0637 | 633 |

10. A fastening system comprising the mechanical fastener of claim 1 and a loop material for engaging with the mechanical fastener.

11. The fastening system of claim 10, wherein the loop material has a fiber basis weight in a range from 10 grams per square meter to 30 grams per square meter.

12. The fastening system of claim 11, wherein the loop material has a fiber basis weight in a range from 20 grams per square meter to 30 grams per square meter, and wherein the mechanical fastener engages with the loop material with a shear strength of at least 2000 gram-force.

13. An absorbent article comprising the mechanical fastener of claim 1.

14. The absorbent article of claim 13, further comprising a front waist region and a rear waist region, wherein at least one of the front waist region or the rear waist region comprises the mechanical fastener, and wherein at least one of the front waist region or the rear waist region comprises a loop material having a fiber basis weight in a range from 10 grams per square meter to 20 grams per square meter.

15. The absorbent article of claim 13, wherein the absorbent article is a pants-style diaper, and wherein the mechanical fastener is located on a tab on a seam or side panel portion of the pants-style diaper.

16. An absorbent pad having at least a top sheet, an absorbent core, and a back sheet, wherein the back sheet comprises the mechanical fastener of claim 1.

17. The absorbent pad of claim 16, wherein the absorbent pad is attached to a top sheet of a diaper or attached to an undergarment.

18. The absorbent pad of claim 16, wherein the thermoplastic backing has a thickness in a range from 40 micrometers to 75 micrometers, and wherein the upstanding fastening elements have a height in a range from 150 micrometers to 300 micrometers and a cap diameter in a range from 190 micrometers to 320 micrometers, wherein the cap extends an overhang distance beyond the post in a range from 5 micrometers to 65 micrometers.

19. The mechanical fastener of claim 1, wherein at least a portion of the post decreases in size from the proximal end to the distal end.

20. The mechanical fastener of claim 1, wherein at least a portion of the cap is turned down toward the thermoplastic backing.

* * * * *

(12) INTER PARTES REVIEW CERTIFICATE (2700th)

United States Patent
Gorman et al.

(10) Number: US 10,165,833 K1
(45) Certificate Issued: Apr. 29, 2022

(54) MECHANICAL FASTENER, FASTENING SYSTEM, AND DISPOSABLE ABSORBENT ARTICLE

(71) Applicants: Michael R. Gorman; Tadato Oritani; Neelakandan Chandrasekaran; Timothy P. Pariseau; Shin Katoh; Zhiqun Zhang

(72) Inventors: Michael R. Gorman; Tadato Oritani; Neelakandan Chandrasekaran; Timothy P. Pariseau; Shin Katoh; Zhiqun Zhang

(73) Assignee: 3M INNOVATIVE PROPERTIES COMPANY

Trial Number:

IPR2020-00699 filed Mar. 10, 2020

Inter Partes Review Certificate for:

Patent No.: 10,165,833
Issued: Jan. 1, 2019
Appl. No.: 14/344,648
Filed: Mar. 13, 2014

The results of IPR2020-00699 are reflected in this inter partes review certificate under 35 U.S.C. 318(b).

INTER PARTES REVIEW CERTIFICATE
U.S. Patent 10,165,833 K1
Trial No. IPR2020-00699
Certificate Issued Apr. 29, 2022

AS A RESULT OF THE INTER PARTES REVIEW PROCEEDING, IT HAS BEEN DETERMINED THAT:

Claim 12 is found patentable.

Claims 1-11 and 13-20 are cancelled.

\* \* \* \* \*